United States Patent
Okada

(10) Patent No.: US 6,234,957 B1
(45) Date of Patent: May 22, 2001

(54) ELECTRONIC ENDOSCOPE SYSTEM CAPABLE OF ENHANCING LUMINANCE

(75) Inventor: Fujio Okada, Omiya (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/245,328

(22) Filed: Feb. 5, 1999

(30) Foreign Application Priority Data

Feb. 9, 1998 (JP) .................................................. 10-042837

(51) Int. Cl.⁷ .................................................. A61B 1/045
(52) U.S. Cl. ............................ 600/109; 600/160; 348/76
(58) Field of Search .............................. 600/109; 348/65, 348/76, 68, 69, 216

(56) References Cited

U.S. PATENT DOCUMENTS

| | | | |
|---|---|---|---|
| 5,010,413 | * 4/1991 | Bahr | 358/242 |
| 5,929,900 | * 7/1999 | Yamanaka et al. | 348/65 |
| 6,100,920 | * 8/2000 | Miller et al. | 348/68 |

FOREIGN PATENT DOCUMENTS 55-43684 * 3/1980 (JP) ...................................... 345/133

* cited by examiner

*Primary Examiner*—John P. Leubecker
(74) *Attorney, Agent, or Firm*—Snider & Associates; Ronald R. Snider

(57) ABSTRACT

An electronic endoscope system that provides, even when it uses a halogen lamp, an image having a brightness equal to that of an image obtained with a xenon lamp. The electronic endoscope system leads rays emitted from a halogen lamp to the tip of an electronic endoscope through a light guide, picks up an internal image of an object to be observed with a CCD through an objective optical system and reads out twice each of an odd field signal and an even field signal successively when a slow scan mode is selected. The odd or even field signal from each field is delayed by a delay memory in a luminance enhancement circuit, and the same field signals are added by an adder. The electronic endoscope system performs image processing of an addition signal thus obtained as a single odd or even field signal, thereby being capable of enhancing the luminance signal, for example, to a level twice as high.

4 Claims, 5 Drawing Sheets

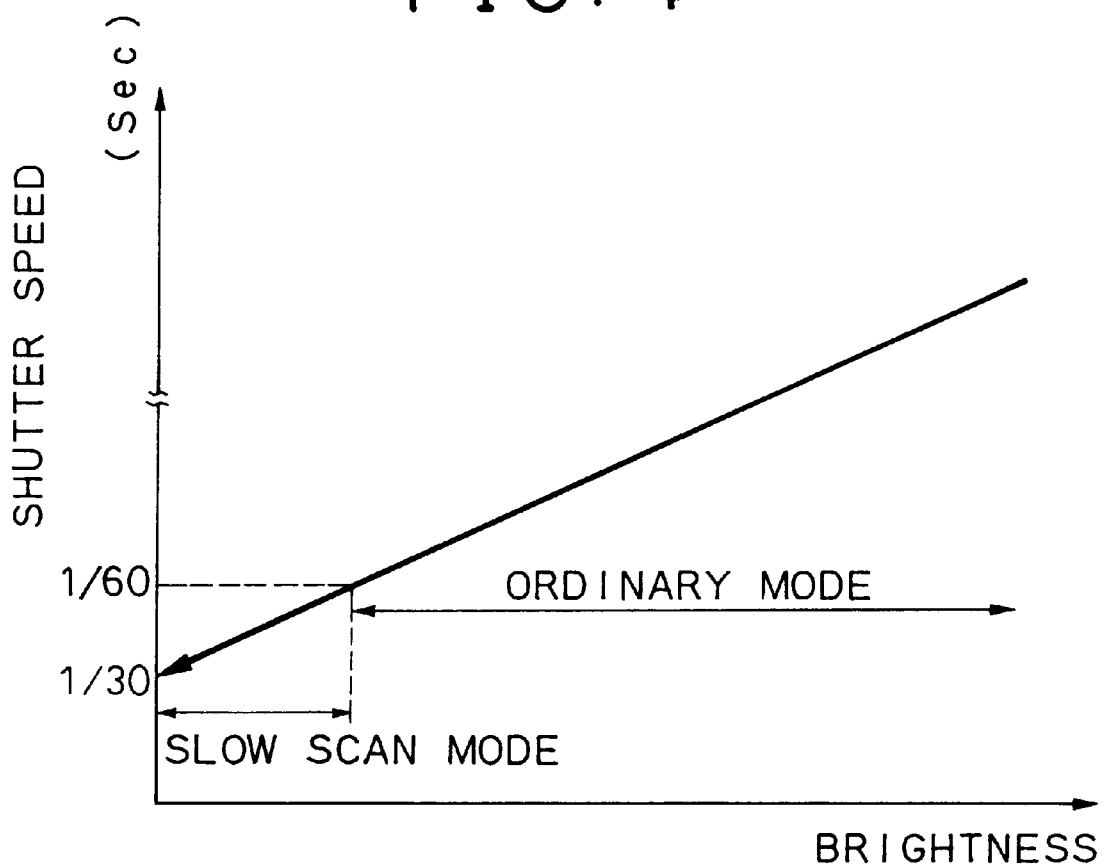

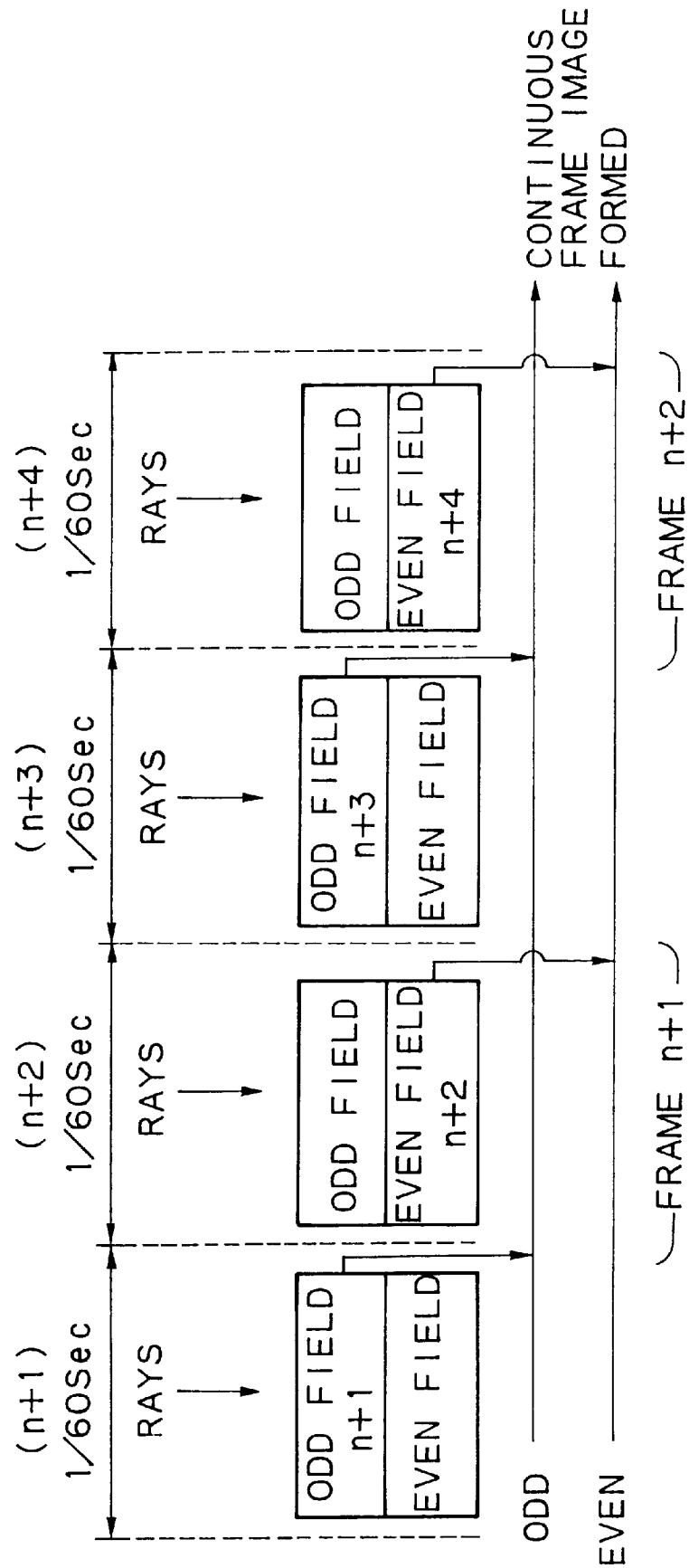

ELECTRONIC ENDOSCOPE SYSTEM CAPABLE OF ENHANCING LUMINANCE

BACKGROUND OF THE INVENTION

This application claims the priority of Japanese Patent Application No. 10-42837 filed on Feb. 9, 1998 which is incorporated herein by reference.

1. Field of the Invention

The present invention relates to an electronic endoscope system, and more specifically to an electronic endoscope system which is configured as a whole so as to be capable of ensuring a predetermined brightness with a halogen lamp in particular used as a light source.

2. Description of the Prior Art

An electronic endoscope system supplies rays from a light source such as a xenon lamp or a halogen lamp to a tip of an electronic endoscope through a light guide and captures an internal image of an object to be observed with an image pickup device, for example, a CCD (charge coupled device) by projecting the rays from the tip into the object to be observed. Video signals which are to be used, for example, as odd field data and even field data are sequentially read from the CCD, subjected to processing such as amplification, white balance and gamma compensation, and are stored in a memory. The video signals are then read out of the memory to display an internal image of the object to be observed on a monitor or the like.

FIG. 5 shows a condition for reading out field signals from the CCD mentioned above. Accumulated electric charges (corresponding to picture elements) are read out from the CCD generally at intervals of a vertical synchronous period (field period) of 1/60 second. Odd field signals and even field signals are read out alternately, for example, as shown in FIG. 5: an odd field signal (data) for a period of n+1 (1/60 second), an even field signal for a period of n+2, an odd field signal for a period of n+3 and an even field signal for a period of n+4.

Though electric charges on odd lines and even field lines of the CCD can be read out as odd field signals and even field signals respectively, the color-difference line sequential mixture readout system adds electric charges accumulated on an upper line to those accumulated on a lower line, thereby reading out mixture signals of (0+1) line, (2+3) line, . . . , for example, as odd field signals and mixture signals of (1+2) line, (3+4) line, . . . as even field signals.

The field signals of the periods n+1 and n+2 are used to form an n+first frame, whereas the field signals of the periods n+3 and n+4 are used to form an n+second frame, whereby an internal image of an object to be observed is displayed on the monitor by interlace scanning of these field signals.

BRIEF SUMMARY OF THE INVENTION

Though the electronic endoscope system described above uses a xenon lamp or a halogen lamp as a light source, the halogen lamp emits rays in an amount as small as 1/8 of that of rays emitted from the xenon lamp. When a halogen lamp is to be used as a light source, it is therefore necessary to configure an electronic endoscope system as a whole so as to maintain the brightness of the image at a predetermined level.

When the electronic endoscope system is to be used for observing an object which is located a relatively short distance from the tip of an electronic endoscope, the halogen lamp poses no problem, but when the electronic endoscope system is to be used for observing an object which is deep and far away, the amount of rays emitted from the halogen lamp is often insufficient, thereby obliging the use of a compensation measure.

The present invention has been made in view of the problem described above and has a primary object of providing an electronic endoscope system which is capable of forming, even with a halogen lamp, an image as bright as one which is formed with a xenon lamp.

SUMMARY OF THE INVENTION

To accomplish the object described above, the electronic endoscope system according to the present invention is characterized in that it comprises a light source unit that uses a halogen lamp as a light source and that leads rays emitted from the halogen lamp to the tip of an electronic endoscope through a light guide, an image pickup device that picks up an internal image of an object to be observed by way of an objective optical system while irradiating the object with illuminating rays from the light source unit, and a signal processing means that adds video signals at one and the same picture element location read out sequentially from the image pickup device in different periods and processes an addition signal as a single video signal.

Another electronic endoscope system according to the present invention is characterized in that it comprises a light source unit that uses a halogen lamp as a light source and that leads rays emitted from the halogen lamp to the tip of an electronic endoscope through a light guide, an image pickup device that picks up an internal image of an object to be observed by way of an objective optical system while irradiating the object with illuminating rays from the light source, an image pickup device driving circuit that reads out one and the same field signal successively at least twice from the image pickup device, a luminance enhancement circuit consisting of a delay circuit that delays a field signal read out from the image pickup device for a predetermined time and an adder which adds a field signal output from the delay circuit to the same field signal read out from the image pickup device, and a signal processing means that processes an output from the luminance enhancement circuit as a single field signal.

Furthermore, the electronic endoscope system according to the present invention may include a switching control means that selects whether or not the luminance enhancement circuit is to be used so that the image pickup device driving circuit can drive the image pickup device to read out one and the same field signal successively when the luminance enhancement circuit is used selectively or to read out an odd field signal and an even field signal alternately when the luminance enhancement circuit is not used selectively.

Furthermore, the electronic endoscope system according to the present invention may include a function of an electronic shutter that controls the exposure time of the image pickup device so that the signal processing means selectively uses an output from the luminance enhancement circuit as a video signal for a slow scan mode in which a shutter speed is slower than the minimum speed of the electronic shutter.

The electronic endoscope system that has the configuration described above is capable of reading out each of the signals of an odd field signal and an even field signal twice from the image pickup device, and adding two data sets for one and the same field (for the odd field and the even field) with the delay circuit and the adder. As a result, the electronic endoscope system is capable of providing a luminance signal multiplied to a level (brightness) twice as high.

Even if the slowest shutter speed is set at 1/60 second, for example, while brightness is being controlled with the function of the electronic shutter, the electronic endoscope system is capable of providing an exposure which is the same as that at a shutter speed of 1/30 second (in the slow scan mode), since it is capable of providing a luminance signal twice as high by executing luminance enhancement processing at a shutter speed of 1/60 second.

BRIEF DESCRIPTION OF THE DRAWINGS

FIG. 4 is a graph illustrating a shutter speed to be set in a second embodiment of the present invention; and FIG. 5 is a diagram illustrating video signal processing in a conventional electronic endoscope.

DETAILED DESCRIPTION OF THE PREFERRED EMBODIMENTS

First Embodiment

Figure 1:
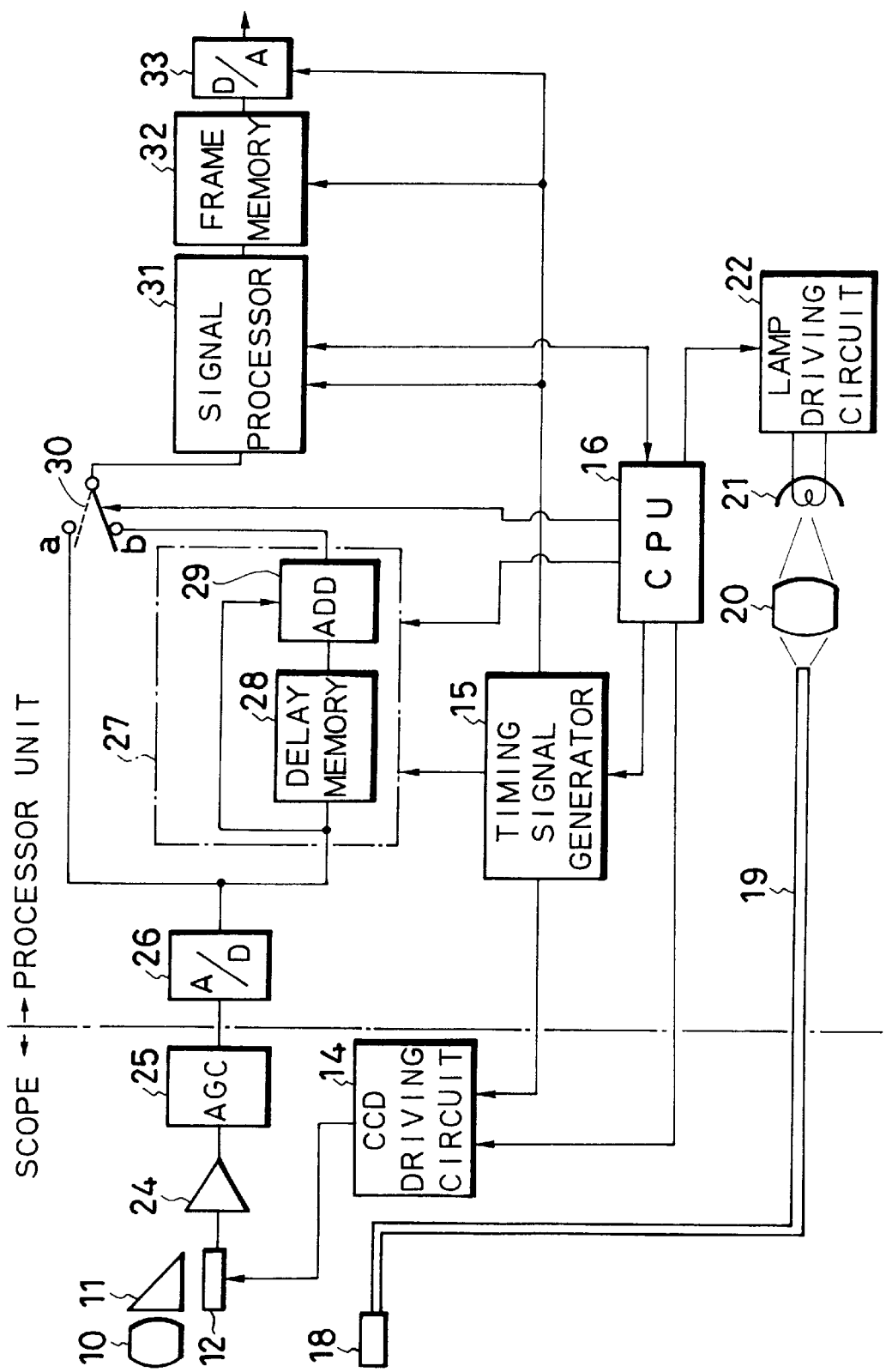
FIG. 1 is a block diagram illustrating a configuration of an electronic endoscope system preferred as a first embodiment of the present invention.

FIG. 1 shows a configuration of an electronic endoscope system preferred as a first embodiment of the present invention. The electronic endoscope system consists of a scope (electronic endoscope) and a processor unit incorporating a light source unit that may be separated from the processor unit. In FIG. 1, an objective optical system 10 is disposed in the tip of the scope and is connected by way of a prism 11 to a CCD 12 which is used as a solid-state image pickup device.

Connected to the CCD 12 is a CCD driving circuit 14 that reads out and controls electric charges accumulated as image data. The CCD driving circuit 14 is equipped with the function of an electronic shutter and is capable of controlling exposure, for example, by selecting shutter speeds within a range from 1/20000 second to 1/60 second. When a slow scan mode is selected, the CCD driving circuit 14 fixes the shutter speed at 1/60 second. A timing signal is supplied from a timing generator 15 to the CCD driving circuit 14.

Furthermore, a CPU 16 is disposed to control the various functions of the electronic endoscope system as a whole.

On the other hand, an illumination window 18 is disposed in the vicinity of the objective optical system 10, a light guide 19 is attached to the illumination window 18 and a halogen lamp 21 is optically connected to the light guide 19 by way of a light source side condenser lens 20 or the like. In addition, a lamp driving circuit 22 is disposed to ignite or drive the halogen lamp 21.

An automatic gain control circuit (AGC) 25 is disposed for the CCD 12 by way of an amplifier 24, and the AGC 25 can be equipped with a correlating duplex sampling circuit (CDS) or the like. At a stage subsequent to the AGC 25, an A/D converter 26 is disposed in the processor unit and a luminance enhancement circuit 27 that is capable of executing the slow scan mode is connected to the A/D converter 26. The luminance enhancement circuit 27 consists of a delay memory 28 that delays a video signal for a field period (vertical synchronous period) of 1/60 second and an adder (ADD) 29 which adds the output from the delay memory 28 to the output from the A/D converter 26 mentioned above. On the basis of controls by the CPU 16, the luminance enhancement circuit 27 adds two odd field signals and two even field signals obtained at different periods, thereby enhancing the luminance signal to be twice as high.

Disposed at a stage subsequent to the luminance enhancement circuit 27 is a switching circuit 30 that selects an output from the luminance enhancement circuit 27 or an output from the A/D converter 26. When brightness is judged to be insufficient even at the slowest shutter speed, a terminal a is switched to a terminal b in the switching circuit 30 on the basis of control performed by the CPU 16, whereby the output from the luminance enhancement circuit 27 is selected.

A signal processing circuit 31 that performs various processes such as gamma compensation, a frame memory 32, and a D/A converter 33 are connected to the switching circuit 30 so that data in odd fields and even fields is stored into the frame memory 32, and subsequently read out and output to a monitor by way of the D/A converter 33. The signal processing circuit 31 generates a luminance signal and supplies it to the CPU 16. The CPU 16 judges the brightness of an image from the luminance signal and outputs a shutter control signal to the CCD driving circuit 14. On the basis of the shutter control signal, the CCD driving circuit 14 sets a shutter speed (exposure time), thereby controlling brightness of the image to a constant level.

Functions of the embodiment that is configured as described above will be described with reference to FIG. 2. When the halogen lamp 21 shown in FIG. 1 is driven or ignited by the lamp driving circuit 22, rays are supplied to the tip of the electronic endoscope through the light guide 19 and projected from the illumination window 18 of the tip. The interior of an object to be observed, which is irradiated with the illumination rays, is captured by the CCD 12 through the objective lens system 10 and electric charges corresponding to imaged rays are accumulated in the CCD 12. The accumulated electric charges are read out by the CCD driving circuit 14 as image data.

When the slow scan mode is not selected, odd field signals and even field signals are read out alternately at intervals of a vertical synchronous period of 1/60 second in the conventional mode and supplied to the signal processing circuit 31 by way of the terminal a in the switching circuit 30, whereby an internal image of the object to be observed is displayed on the monitor. In this case, the CCD 12 is exposed at a shutter speed of 1/20000 second to 1/60 second.

When the brightness of an image is insufficient and the CPU 16 selects the slow scan mode, an odd field signal is read out twice successively at intervals of the vertical synchronous period of 1/60 second and then an even field signal is read out twice successively from the CCD 12, whereafter the signal readout is repeated. These field signals are subjected to gain processing in the automatic gain control circuit 25 and supplied through the A/D converter 26 into the luminance enhancement circuit 27, which adds the two same field signals.

Figure 2:
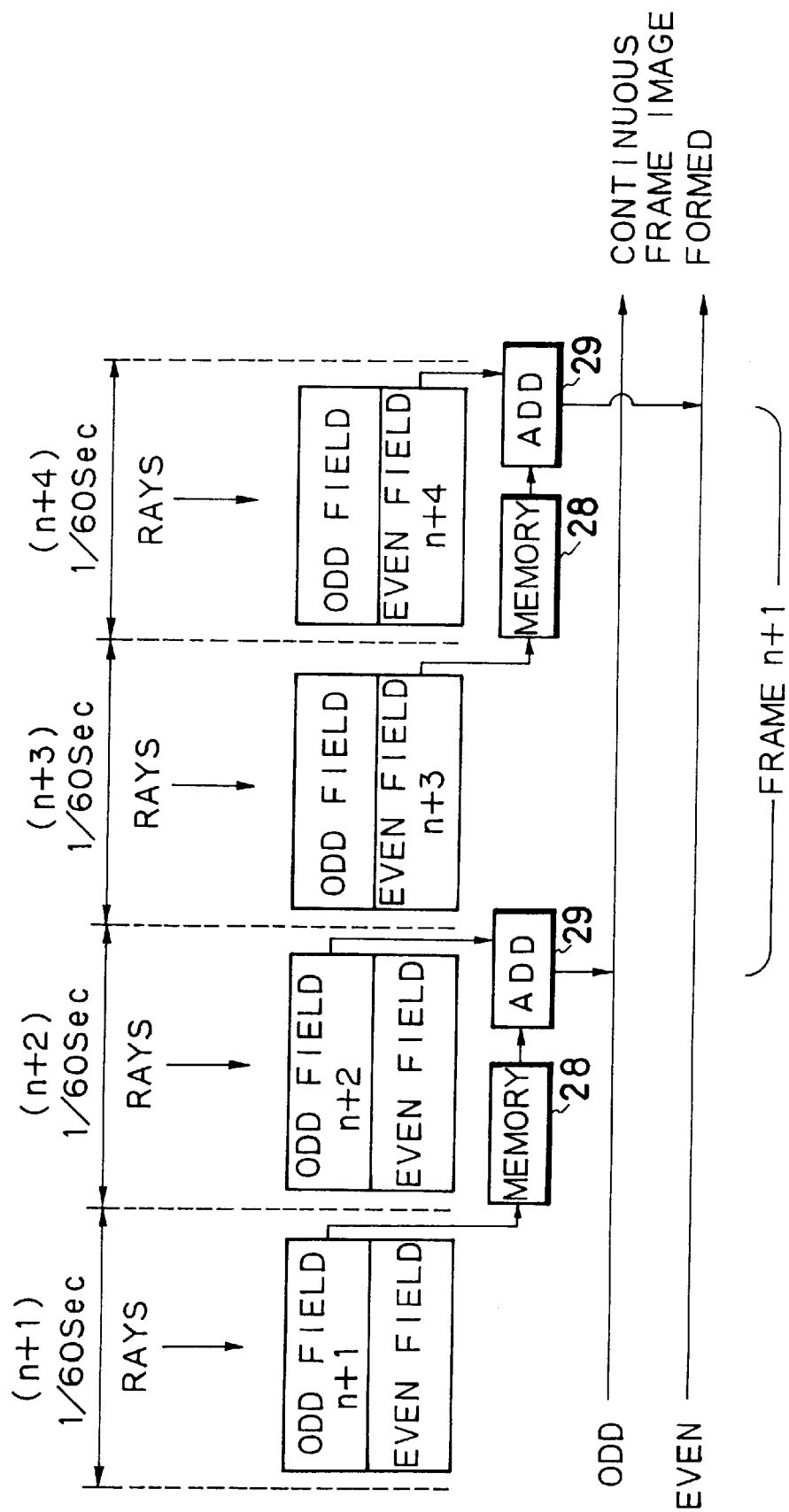
FIG. 2 is a diagram descriptive of luminance enhancement processing in the embodiment of the present invention.

FIG. 2 visualizes a concept of the signal processing in the circuits from the CCD 12 to the luminance enhancement circuit 27. When vertical synchronous periods from n+1 to n+4 (1/60 second) are considered, as in the case shown in FIG. 4, for example, odd field signals obtained by exposure in the period of n+1 are stored into the memory 28 and thereafter supplied to the adder 29. Then, the odd field signals are read out again by exposure in the next period of n+2 and input directly into the adder 29. Accordingly, the adder 29 duplexly adds the odd field signals that are output in different periods.

By exposure in the period of n+3, even field signals are read out and stored into the memory 28. Also by exposure in the next period of n+4, even field signals are read out again and input directly into the adder 29. Accordingly, the adder 29 adds the even field signals which are obtained similarly in different periods. As a result, an odd field signal and an even field signal at levels (amplitudes) twice as high as those of the ordinary signals are obtained as n+first frame signals and supplied to the signal processing circuit 31 by way of the terminal b in the switching circuit 30.

The signal processing circuit 31, which generates a color-difference signal and a luminance signal, for example, provides as the luminance signal a signal that has an amplitude twice as wide as that of the conventional luminance signal. A video signal output from the signal processing circuit 31 is stored into the frame memory 32 and then output to the monitor by way of the D/A converter 33.

Figure 3:
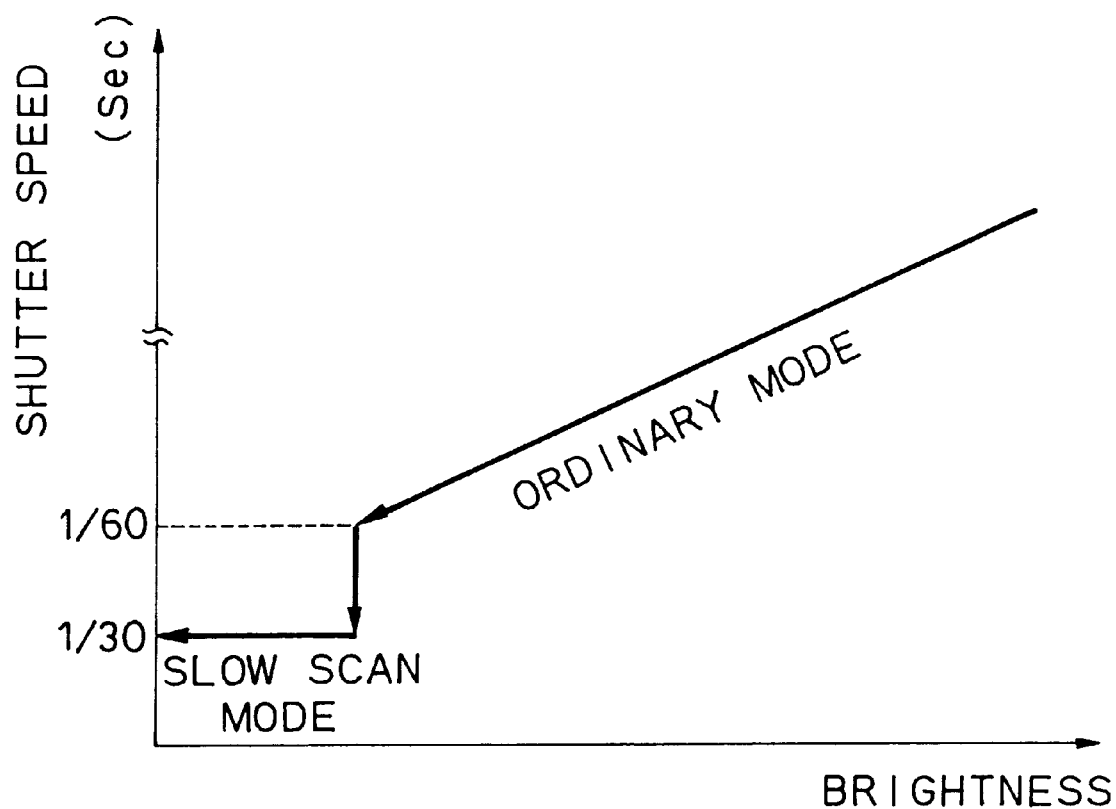
FIG. 3 is a graph illustrating a shutter speed to be set in the first embodiment of the present invention.

In the slow scan mode, in which the same data is added duplexly as described above, the electronic endoscope system is capable of obtaining a luminance signal at a level twice as high, that is, a brightness twice as high, thereby allowing the slowest shutter speed of $1/30$ second to be realized as shown in FIG. 3. That is, when the electronic endoscope system carries out luminance enhancement processing at a shutter speed of $1/60$ second, which is the slowest within a range from $1/20000$ second to $1/60$ second, for example, that can be set by the shutter driving circuit 14 for the electronic shutter described above, the electronic endoscope system slows down the shutter speed to $(1/60) \times 2 = 1/30$, thereby performing exposure at a slowest shutter speed of $1/30$ second.

When the numerical aperture (NA) of the light guide 18 is enlarged to improve the illuminating rays, the optical performance of the objective optical system 10 is upgraded and the sensitivity of the CCD 12 is made higher in addition to the luminance enhancement (twice as high) by the luminance enhancement circuit 27 described above. The embodiment thus makes it possible to obtain rays in an amount eight times as large as that of rays available with the conventional electronic endoscope system, or equal to that of rays obtainable with a xenon lamp.

Usable as the odd and even field signals mentioned above are signals that are obtained directly from odd and even lines of the CCD 12 as described above, signals that are formed by adding signals from picture elements on upper and lower lines at different locations as in a color-difference line sequential mixture readout system or signals that are processed otherwise.

Though one and the same field signal is added twice in the embodiment described above, the addition may be repeated three or more times and it can also be made to use, in place of the halogen lamp, an LED which has high luminance as a light source.

As understood from the foregoing description, the electronic endoscope system according to the present invention is capable of multiplying an amplitude of a luminance signal and providing an image that has a brightness as a whole that is equal to that of an image available with a xenon lamp when it is configured to improve the functions of its component members. Furthermore, the electronic endoscope system according to the present invention, which is equipped with the function of an electronic shutter, provides, the advantage of providing a slow scan mode in which the shutter speed is slowed down to $1/2$ of the ordinary minimum shutter speed.

Second Embodiment

FIG. 4 shows a shutter speed to be set in the second embodiment of the execution patterns. In this second embodiment, the shutter speed was set to be able to continuously change even in the slow scan mode. To be more specific, when CPU16, which has evaluated insufficient brightness, is switched to the slow scan mode in the circuitry of FIG. 1, for example, if the values within a range from $1/120$th second to $1/60$th second are set in sequence by the CCD drive circuit 14 with the electronic shutter function, the shutter speed can continuously be changed as shown in FIG. 4.

For example, if the shutter speed is made slower by setting the said speed at $1/100$th second, $1/90$th second, $1/80$th second and $1/70$th second in sequence, it is substantially made possible to control an exposure amount at the shutter speeds of $1/50$th second, $1/45$th second, $1/40$th second and $1/35$th second by an overlap addition processing of the luminance signals above. According to such second example, there is an advantage over capability of minutely controlling exposure, compared with the case of FIG. 3 where the substantial shutter speed is fixed at $1/30$th second.

What is claimed is:

1. An electronic endoscope system comprising:
    a light source unit that uses a halogen lamp as a light source and leads rays emitted from said halogen lamp to the tip of an electronic endoscope through a light guide;
    an image pickup device that picks up, through an objective optical system, an internal image of an object to be observed when the object is irradiated with illuminating rays from said light source unit;
    an image pickup device driving circuit that reads out one field signal successively at least twice from said image pickup device;
    a luminance enhancement circuit consisting of a delay circuit that delays the field signal read from said image pickup device for a predetermined time and an adder that adds a field signal output from said delay circuit to the same field signal read from said image pickup device; and
    a signal processing means that possesses an output from said luminance enhancement circuit as a single field signal.

2. An electronic endoscope system according to claim 1,
    wherein said electronic endoscope system includes a switching control means which selects whether or not said luminance enhancement circuit is to be used, and
    wherein said image pickup device driving circuit drives said image pickup device so as to read out one field signal successively when said luminance enhancement circuit is used selectively or an odd field signal and an even field signal alternately when said luminance enhancement circuit is not used selectively.

3. An electronic endoscope system according to claim 1,
    wherein said image pickup device driving circuit provides the function of an electronic shutter which controls the exposure time of said image pickup device, and
    wherein said signal processing means selectively uses an output from said luminance enhancement circuit, thereby forming a video signal for a slow scan mode in which the shutter speed is made slower than the slowest speed of said electronic shutter.

4. An electronic endoscope system according to claim 3,
    wherein said signal processing means for obtaining the shutter speed, which is slower than minimum speed of the electronic shutter function, is set to continuously change by using a luminance enhancement circuit in the slow scan mode.

* * * * *